(12) United States Patent
Brooks

(10) Patent No.: US 7,016,467 B2
(45) Date of Patent: Mar. 21, 2006

(54) MOBILE DIGITAL RADIOGRAPHY X-RAY APPARATUS AND SYSTEM

(76) Inventor: Jack Jerome Brooks, P.O. Box 1074, 116 W. Huron Ave., Folly Beach, SC (US) 29439

( * ) Notice: Subject to any disclaimer, the term of this patent is extended or adjusted under 35 U.S.C. 154(b) by 0 days.

(21) Appl. No.: 10/918,267

(22) Filed: Aug. 13, 2004

(65) Prior Publication Data

US 2006/0034427 A1 Feb. 16, 2006

(51) Int. Cl.
*H05G 1/00* (2006.01)

(52) U.S. Cl. ........................... 378/102; 378/198
(58) Field of Classification Search ................ 378/102, 378/55, 62, 116, 196–198; 709/220–221
See application file for complete search history.

(56) References Cited

U.S. PATENT DOCUMENTS

| | | | |
|---|---|---|---|
| 5,514,873 A * | 5/1996 | Schulze-Ganzlin et al. | 250/394 |
| 5,608,774 A | 3/1997 | Polichar et al. | |
| 5,835,558 A * | 11/1998 | Maschke | 378/198 |
| 5,877,501 A | 3/1999 | Ivan et al. | |
| 6,234,672 B1 * | 5/2001 | Tomasetti et al. | 378/197 |
| 6,282,264 B1 | 8/2001 | Smith et al. | |
| 6,326,625 B1 | 12/2001 | Zur | |
| 6,398,409 B1 | 6/2002 | Brooks | |
| 6,574,629 B1 | 6/2003 | Cook, Jr. et al. | |
| 6,575,624 B1 * | 6/2003 | Noegel et al. | 378/198 |
| 6,891,920 B1 * | 5/2005 | Minyard et al. | 378/37 |
| 2002/0150214 A1 * | 10/2002 | Spahn | 378/189 |
| 2003/0219100 A1 * | 11/2003 | Okoda | 378/102 |
| 2004/0146142 A1 * | 7/2004 | Maijala | 378/102 |

OTHER PUBLICATIONS

Parks, E.T., Williamson, G.F., Digital Radiography: An Overview. Journal of Contemporary Dental Practice. Nov. 15, 2002. pp. 23-39. vol. 3, No. 4.
www.amershamhealth.com/medcyclopaedia/medical/Volume%201/digital%20radiography.asp.

* cited by examiner

*Primary Examiner*—David V. Bruce
*Assistant Examiner*—Hoon Song
(74) *Attorney, Agent, or Firm*—Harleston Law FirmLLC; Kathleen M. Harleston

(57) ABSTRACT

A mobile x-ray apparatus for generating a digital x-ray image and transmitting it to a remote site, includes: (a) a first computer; (b) a flat panel detector in communication with the first computer; and (c) an x-ray cart assembly removably supporting the first computer, which includes a cart with a battery charger and an x-ray machine in communication with the flat panel detector; wherein the mobile x-ray apparatus includes an x-ray tube extendible from the cart, and a mechanism for framing a target body area of a patient. Also included herein is a method of generating a digital x-ray image and forwarding it to a remote site using the mobile x-ray apparatus.

9 Claims, 8 Drawing Sheets

MOBILE DIGITAL RADIOGRAPHY X-RAY APPARATUS AND SYSTEM

CROSS REFERENCE TO RELATED DOCUMENT

This invention was described in Disclosure Document Number 541027, which was received by the U.S. Patent & Trademark Office on Oct. 30, 2003.

BACKGROUND OF THE INVENTION

1. Technical Field

The present invention relates to a mobile x-ray apparatus with a flat panel detector, and a diagnostic imaging system and method of rapidly generating and forwarding a digital x-ray image utilizing a computer of the mobile x-ray apparatus and a medical imaging network.

2. Background Information

The latest advent in radiography is Digital Radiography (DR), which is essentially replacing the film-based and Computed Radiography (CR) imaging, because it allows immediate image access and manipulation of images, reduced storage cost, and transmission to remote locations. Digital Radiography also has improved dynamic range, which eliminates the need to capture multiple images of the same anatomy (a common practice in film-based imaging). A flat panel detector employs an array of sensors with a direct or indirect conversion type. In any case, the image is directly transmitted from the flat digital detection panel to the computer, where it is instantaneously processed and displayed. The image may then be enhanced and stored, and later retrieved, or printed. Imaging enhancements include alteration of density (i.e., increasing or decreasing brightness), alternation of contrast (i.e., gradient of gray levels), conversion of the grayscale (i.e., reversing black and white) and magnification.

The patient study may also be sent to local or remote sites, such as the site of an in-house clinician or a distant diagnostic center. Today, efficient image transmission is made possible by the DICOM (Digital Imaging and Communications for Medicine) protocol. The DICOM protocol allows for the development of software for medical imaging devices to transmit and receive medical images across multivendor platforms. The information encapsulated in DICOM package uses TCP/IP and ethernet networking. This combination is referred to as a Picture Archiving and Communication System (PACS) network. The use of ethernet and TCP/IP allows imaging networks to use the existing infrastructure of a facilities LAN (Local Area Network) and/or WAN (Wide Area Network). However, although Digital Radiography far exceeds the limitations of film-based radiography, there are still issues with mobile x-ray apparatuses that must use either CR or film cassettes. In the case of film after the exposure the cassette must be transported to a film developer. After development, the film must be transported to an area where it can be viewed on a light box. With CR, the cassette must be transported to a machine that scans the phosphor plate inside the CR cassette. At this point, the information from the CR cassette can be placed on to the facilities PACS network. In either case, the information is not immediately available to the x-ray technician for evaluation of the image. This is most important in a location such as an ICU (intensive care unit) or an emergency room, where a technician may be looking for information regarding an injury, indwelling catheter, pulmonary condition, or other conditions that may require immediate attention.

Sensor arrays in the form of flat panel x-ray detectors while in use in x-ray rooms in various configurations have yet to be combined with mobile x-ray apparatuses in a way that takes full advantage of the integration with a computer workstation and PACS network on a mobile x-ray apparatus.

Currently available digital radiography apparatuses necessitate travel or transport of x-ray subjects to a designated area equipped with Digital Radiography equipment (e.g., flat panel detector, computer, monitor, printer, x-ray table, etc.). Movement of patients from one area of a medical facility, such as a hospital, to another often causes such patients considerable pain and/or discomfort. Moreover, transportation of patients consumes time and energy, both for the patient and/or the orderly or other workers. Current mobile x-ray apparatuses require the use of film or computed radiography devices, neither of which provides immediate results. There is therefore a need to incorporate a computer controlled flat panel detector with a mobile x-ray machine in order to bring the Digital Radiography devices to the patient. X-ray results would then be immediately available to the technician or other worker for evaluation and transmission on the facilities imaging network.

Additionally, current digital radiography systems possess a cable connecting the computer and the flat panel detector. Cable handling can complicate movement of the flat panel detector and the patient. Care must be taken not to tangle or exceed the length of the cable, for example. There is a need for a Digital or Radiography system that does not require the use of cables. The mobile x-ray apparatus and unique digital radiography system and method of the present invention meet these and other needs.

BRIEF SUMMARY OF THE INVENTION

The present invention is a mobile x-ray apparatus for generating a digital x-ray image and transmitting it to a remote site, which includes:
(a) a first computer;
(b) a flat panel detector in communication with the first computer; and
(c) an x-ray cart assembly removably supporting the first computer, the x-ray cart assembly comprising a battery-powered cart, a battery charger supported on the cart, and an x-ray machine supported by the cart and in communication with the flat panel detector;
wherein the mobile x-ray apparatus comprises an x-ray tube extendible from the battery-powered cart, and a mechanism for framing a target body area of a patient. Also included herein is a method of generating a digital x-ray image and forwarding it to a remote site using the mobile x-ray apparatus.

BRIEF DESCRIPTION OF THE SEVERAL VIEWS OF THE DRAWINGS

A more complete understanding of the invention and its advantages will be apparent from the following detailed description taken in conjunction with the accompanying drawings, wherein examples of the invention are shown, and wherein.

DETAILED DESCRIPTION OF THE INVENTION

Figure 1:
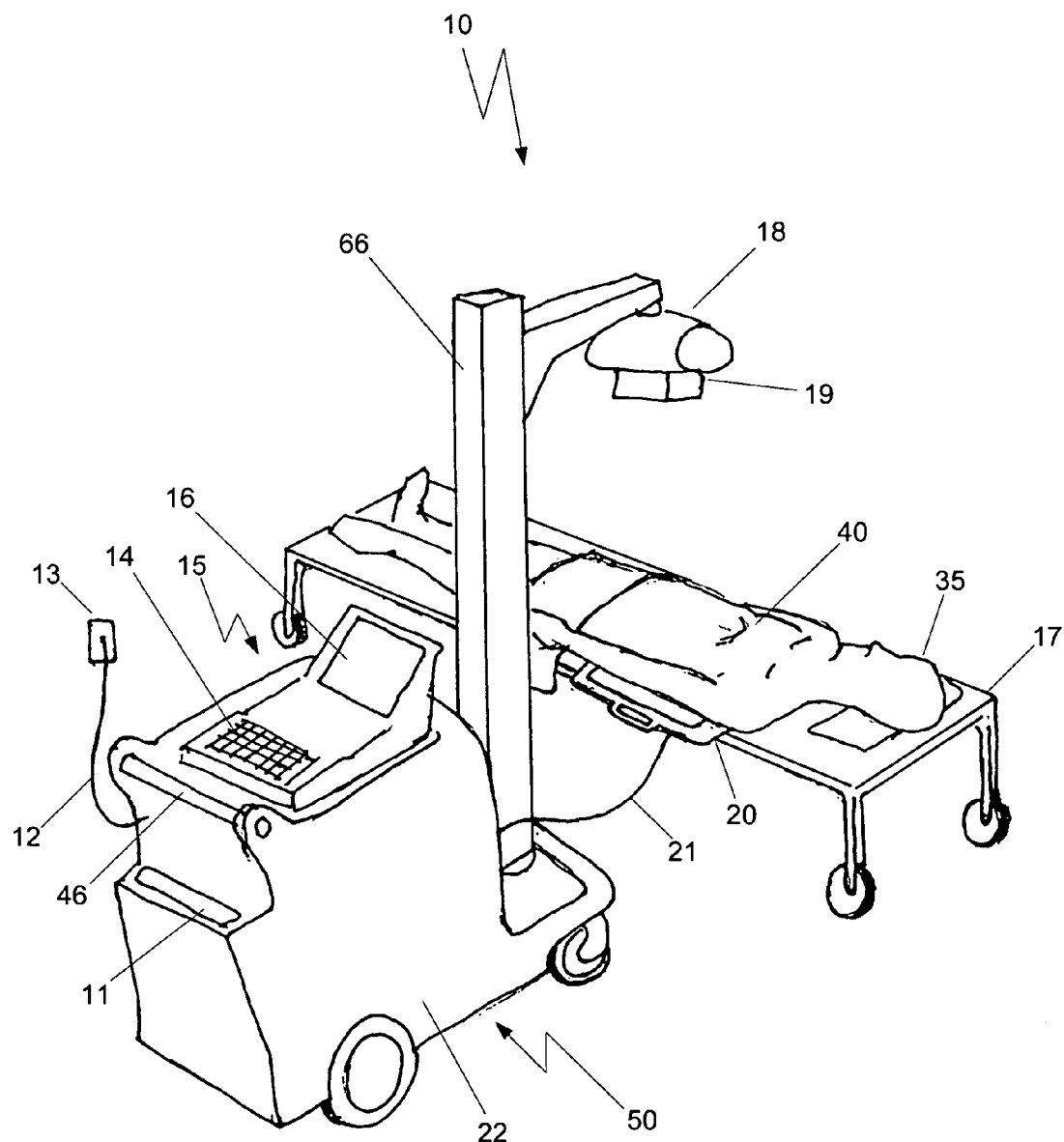
FIG. 1 is a perspective view of a mobile x-ray apparatus according to the present invention, showing a patient in a prone position.

In the following description, like reference characters designate like or corresponding parts throughout the several views. Also, in the following description, it is to be understood that such terms as "front," "back," "within," and the like are words of convenience and are not to be construed as limiting terms. Referring in more detail to the drawings, the invention will now be described.

Figure 2:
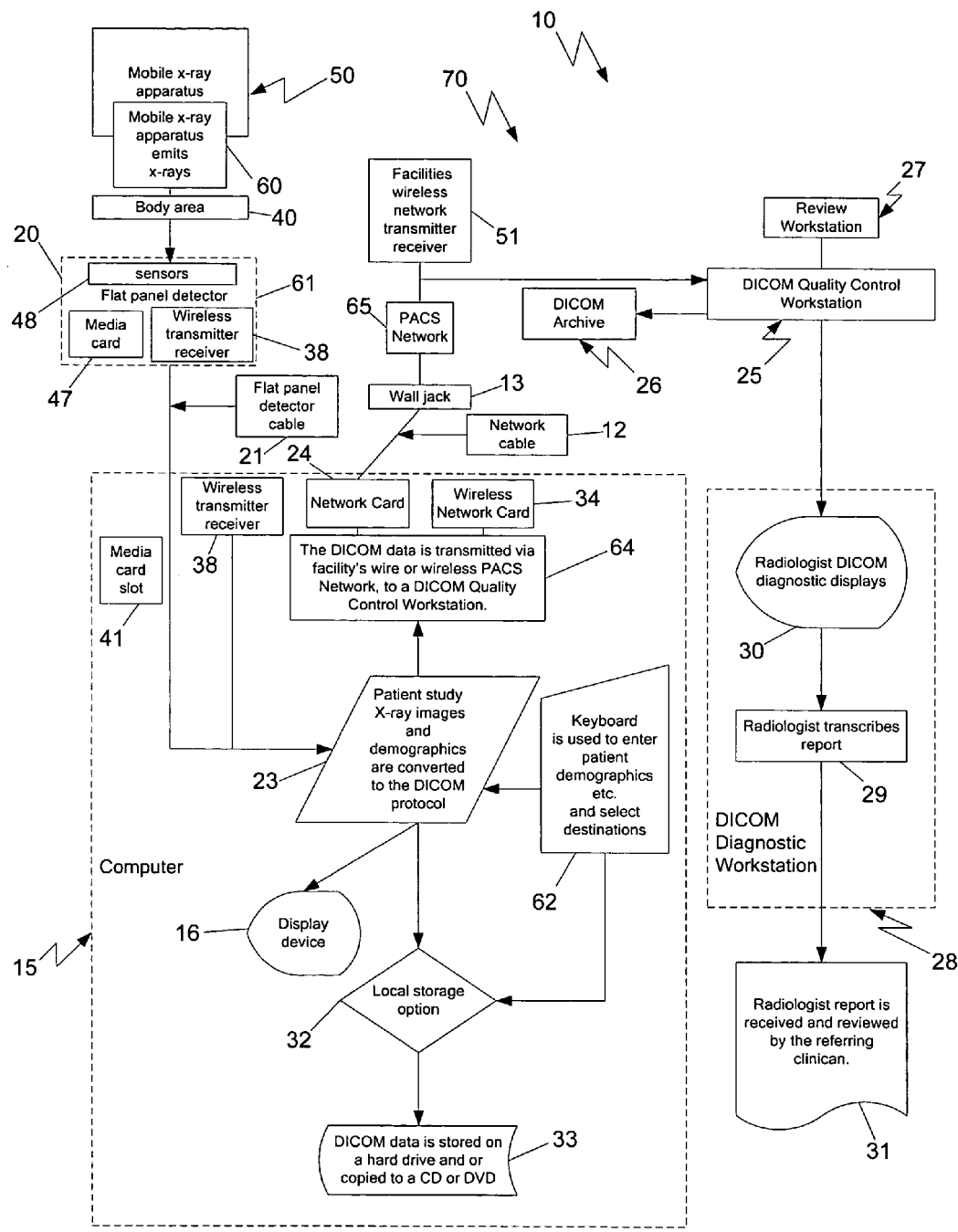
FIG. 2 is a flowchart illustrating a digital medical imaging system and method according to the present invention.

Turning first to FIG. 1, a mobile x-ray apparatus 10 according to the present invention comprises a flat panel detector 20, an x-ray cart assembly 50, and a first computer 15. The mobile x-ray apparatus 10 is suitable for use in a medical facility and in conjunction with a Digital or Radiography (DR) system and method 70, which is schematically depicted in FIG. 2. The flat panel detector 20 is a state-of-the-art Digital and Radiography (DR) flat panel detector with an array of sensors 48, depicted in FIG. 4. The x-ray cart assembly 50 comprises a battery-powered cart 22 that supports the first computer. The x-ray cart assembly 50 has internal batteries, which makes the machine independent of an external power source, and also a battery charger, high-voltage generator, and the electronics necessary to control and produce the proper imaging techniques from the x-ray tube 18. The x-ray tube 18 is supported by an adjustable tube stand 66. An x-ray columnator 19 is used for framing a targeted body area of a patient 35 during the x-ray procedure.

Devices for communications between the flat panel detector 20 and the first computer 15 with various DICOM network destinations, both internal and external to the computer 15, are located on the x-ray cart assembly 50, as shown in the system and method 70 of FIG. 2.

Figure 3:
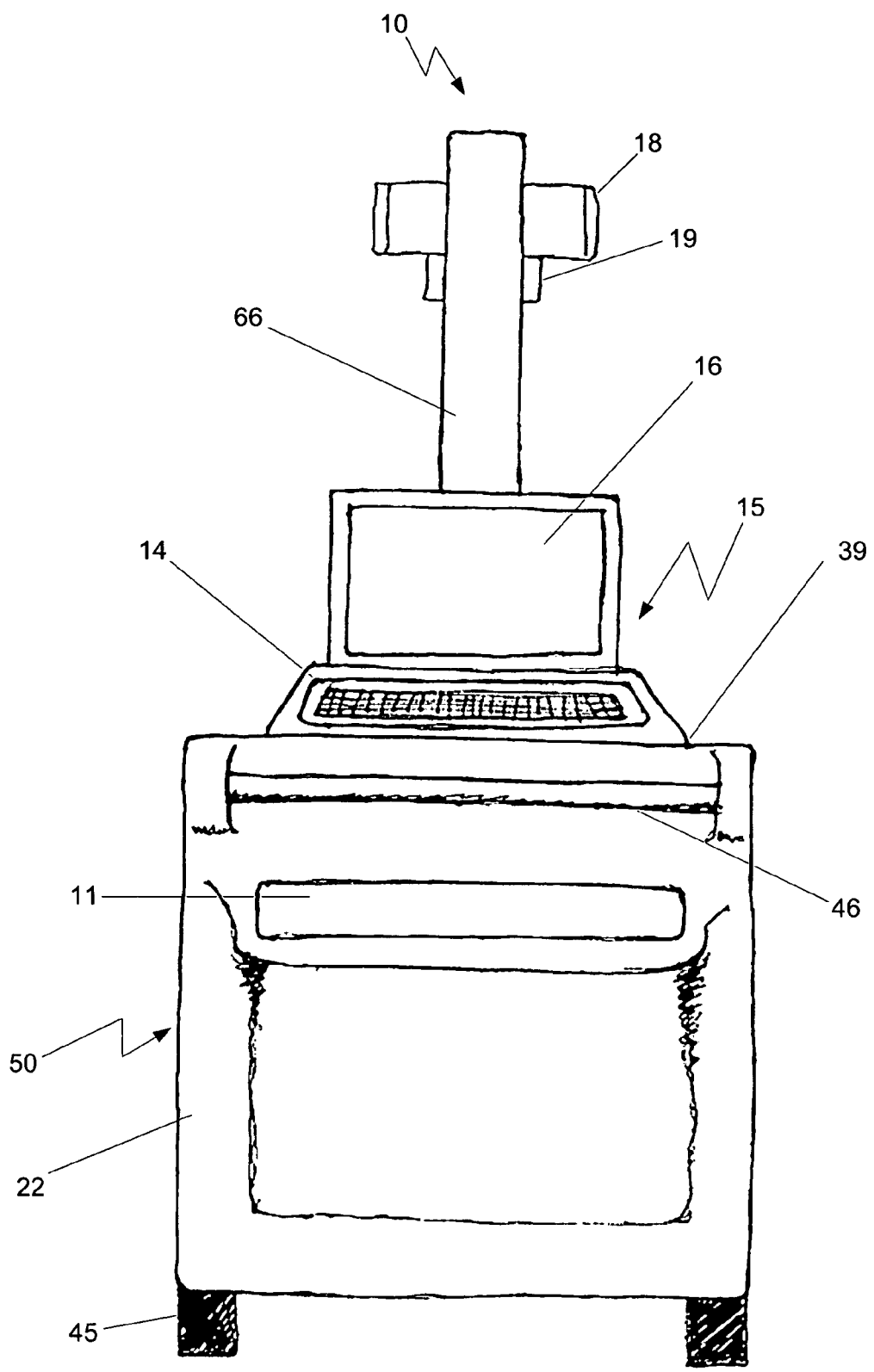
FIG. 3 is a front elevational view of a mobile x-ray apparatus according to the present invention.

Turning next to FIG. 3, the x-ray cart assembly 50 comprises several features that make it quickly and easily movable between different locations. Cart wheels 45 and a push bar 46 extending from the cart allow a user, such as an x-ray technician, an orderly, or other medical employee, to push the cart from one location to another. The cart is preferably motorized and has an electrical drive train. Two of the wheels 45 are drive wheels and two are for steering. The x-ray assembly preferably includes a storage area 11 for removably securing the flat panel detector 20 within the x-ray cart assembly. The cart storage area 11 is most preferably a rigid, vertically oriented pocket, with a removable flat panel detector 20. The cart wheels 45, push bar 46, and flat panel detector storage area 11 advantageously permit the user to move the x-ray cart assembly 50 between various rooms in the medical facility and easily use it to take x-rays in any available area. Potential x-ray sites include a patient's private or shared room, intensive care unit, an area designated for taking x-rays, or an emergency room.

Continuing with FIG. 3, the x-ray cart assembly 50 preferably includes a computer support surface 39 oriented in a generally horizontal plane for supporting the first computer 15. The first computer 15 comprises a first input apparatus 14 for inputting and a first display device 16 for displaying inputted information.

Figure 4:
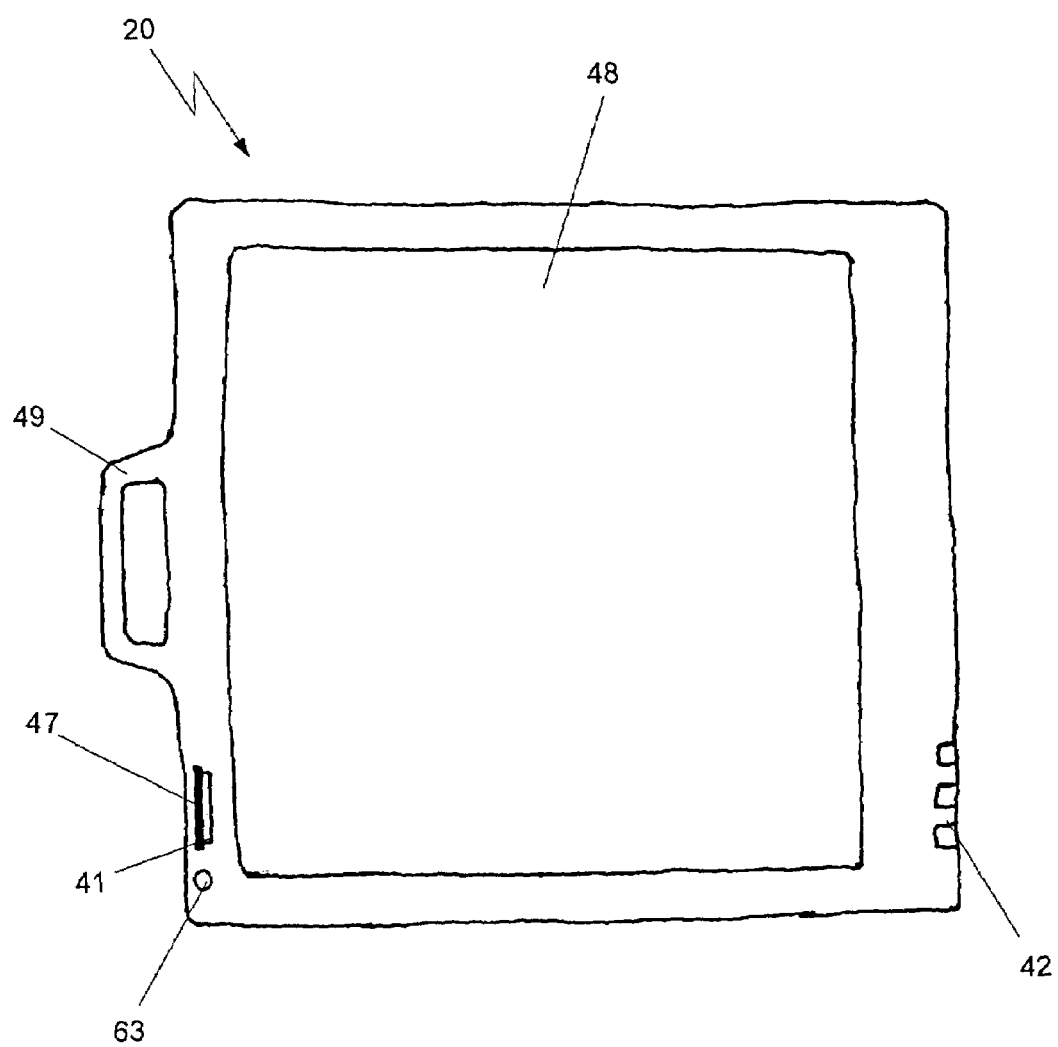
FIG. 4 is an elevational view of a flat panel detector according to the present invention.

Referring to FIG. 4, the flat panel detector 20 comprises an array of direct or indirect sensors 48. The flat panel detector 20 further comprises an internal wireless transmitter receiver, a flat panel detector cable port 63, and/or a media card slot 41 in which a media card 47 is removably inserted. The flat panel detector 20 is preferably battery-powered and has an external battery contact connector 42 for charging batteries internal to the flat panel detector 20 while inserted into the flat panel detector storage area 11. The flat panel detector 20 preferably also comprises a flat panel detector handle 49 to facilitate transport and placement.

In use, the first computer 15 of the mobile x-ray apparatus 10 is the communication center of the digital medical imaging network system 70. The first computer receives data input from the first x-ray technician and the flat panel detector 20 and transmits data to the first x-ray technician, the flat panel detector 20, the x-ray machine assembly, and networking destinations. The first x-ray technician shares information with the flat panel detector 20, the x-ray machine assembly, and networking destinations utilizing the first computer 15 as an intermediary. The first computer 15 communicates with the flat panel detector 20 using a software program and a flat-panel detector cable 21, a wireless network, and/or the media card 47. The first computer 15 communicates with the x-ray machine assembly and the networking destinations using the software program and the network, and with the first x-ray technician by means of the first input apparatus 14 and first display device 16.

The first input apparatus 14 and the first display device 16 are incorporated into the first computer 15, as shown in FIG. 1. According to a preferred embodiment of the mobile x-ray apparatus 10, the first input apparatus 14 and the first display device 16 are a keyboard and a high-resolution liquid crystal display (LCD) monitor, respectively. The first x-ray technician may use the first input apparatus 14 to input networking destinations, enter patient demographic information, set x-ray techniques and the output apparatus to evaluate and manipulate a digital image, view network destinations, and view x-ray apparatus settings. If the digital medical imaging network system 70 utilizes a wire-based network, the first computer 15 comprises a network card 24 and a network cable port or wall jack 13 in order to access the wire-based network. A network cable 12 is removably insertable in the network wall jack. If the digital medical imaging network system 70 utilizes a wireless network, the first computer 15 comprises a wireless network card 34 for accessing the wireless network.

In FIG. 1, the mobile x-ray apparatus 10 is in use with a wire-based network and a flat panel detector cable 21 linking the computer's network port and a network wall jack 13 in the medical or other facility. Similarly, the flat panel detector cable 21 links the first computer 15 and the flat panel detector 20. In order to employ the mobile x-ray machine 50 for radiation, the first x-ray technician positions the flat panel detector 20 underneath or behind the target area 40 of a patient 35 that will be irradiated. FIG. 1 shows the flat panel detector 20 directly underneath a patient's chest. The flat panel detector 20 is supported on a surface 17. The detector 20 is in position for a chest x-ray. The x-ray technician also correctly positions the x-ray tube 18 and the columnator 19 to frame the target body area 40. This may involve vertically translating, horizontally translating, or rotating the x-ray tube 18 and its attached columnator 19. Here, the x-ray tube 18 and columnator 19 are placed directly over the patient's chest, poised for the chest x-ray.

Figure 5:
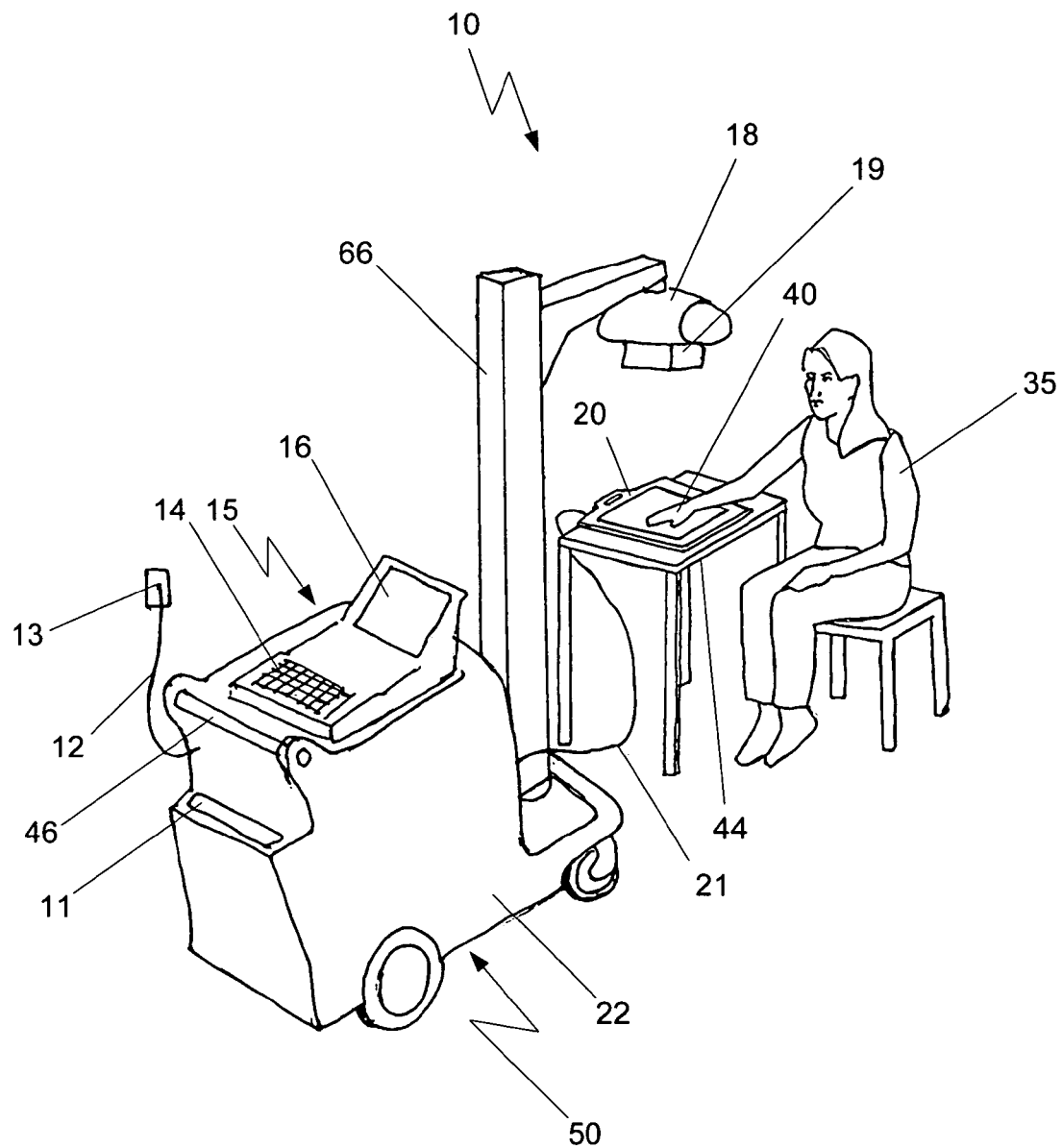
FIG. 5 is a perspective view of a mobile x-ray apparatus according to the present invention, showing a seated patient with an arm on a flat panel detector supported by a table.

While the patient 35 is shown in a prone position in FIG. 1, it is not always possible, desirable, or necessary for the patient 35 to lie down during the irradiation procedure. The patient may not be physically able to lie flat, or it may be extremely painful for the patient to do so. X-ray tables can be quite uncomfortable, and lying on one often makes the patient more nervous. With the present mobile x-ray apparatus and system, it is usually possible to capture an image while the patient sits, stands, leans, etc. In FIG. 5, the patient 35 is in a seated position while the mobile x-ray apparatus 10 is in use. Here, the flat panel detector 20 is supported on a top surface of a small table 44. In FIG. 5, the body area 40 to be examined is the patient's hand, which lies flat on the flat panel detector 20. The x-ray tube 18 and the columnator 19 have been positioned above the subject hand. The x-ray apparatus 10 is oriented for a hand exposure. This illustrates the portability, versatility, and convenience of the mobile x-ray apparatus 10.

Figure 6:
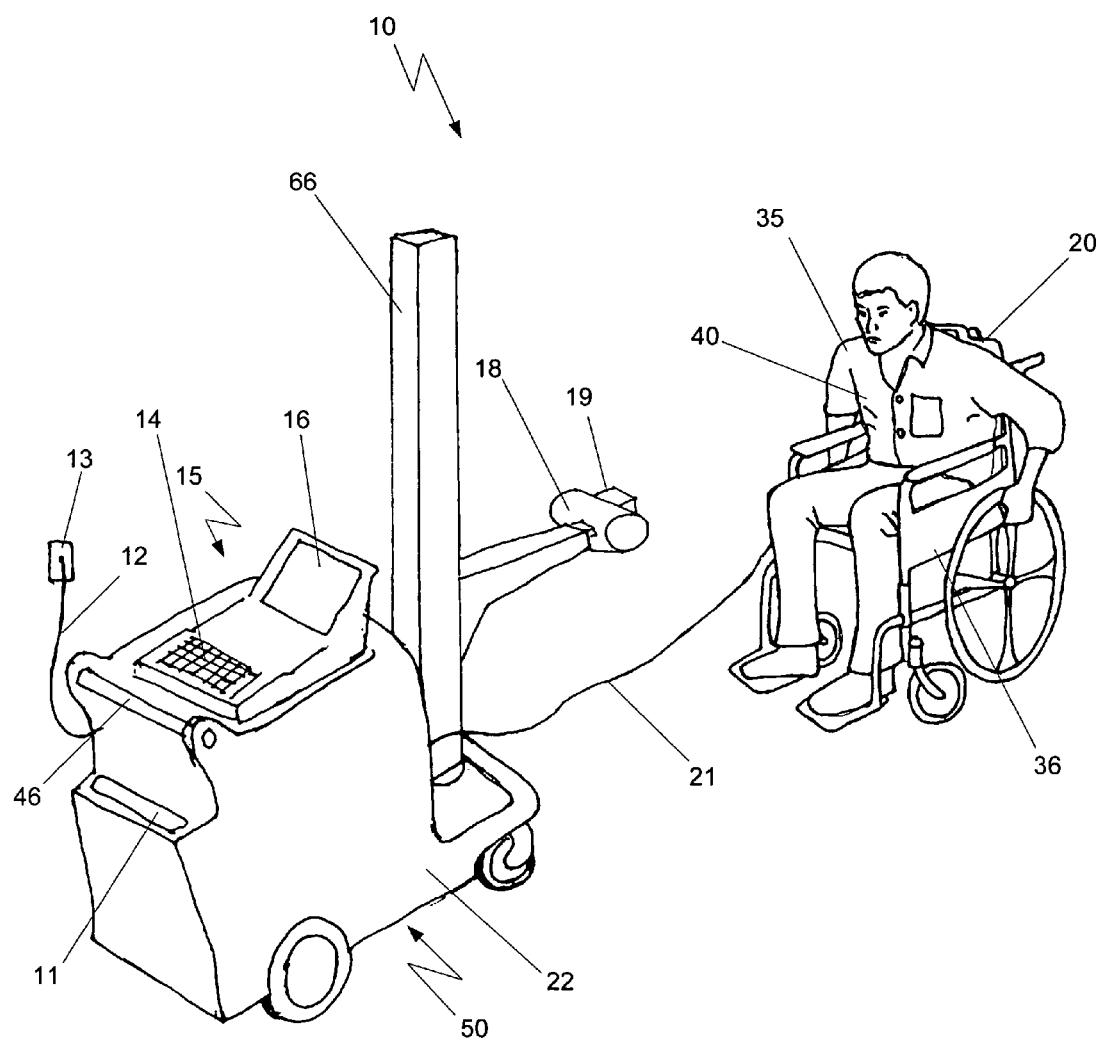
FIG. 6 is a perspective view of a mobile x-ray apparatus according to the present invention, showing a patient seated in a wheelchair with a flat panel detector behind the patient.

Turning to FIG. 6, the x-ray apparatus 10 is shown in use with a patient in a wheelchair 36. This also illustrates the portability, versatility, and convenience of the mobile x-ray apparatus 10. The patient need not exit the wheelchair 36 for the procedure to be performed well. This is advantageous in that it conserves the patient's and x-ray technician's time and physical efforts, which results in cost savings for the hospital and patient. There is also less strain on and less danger for the patient and technician. Here, the patient 35 sits in the wheelchair with the flat panel detector 20 oriented vertically between the patient's back and the backrest of the wheelchair. The patient 35 leans forward a small distance to accommodate the flat panel detector 20. The x-ray tube 18 and the columnator 19 are vertically lowered and rotated so that they point toward the target body area 40, which here is the patient's chest. This illustrates another possible orientation for a chest x-ray. The first computer 15 is connected to a network wall jack 13 by a network cable 12. The flat panel detector 20 is connected to the first computer 15 by a flat panel detector cable 21.

After the flat panel detector 20, x-ray tube 18, columnator 19, and patient 35 are correctly positioned for capture of at least one digital image, the first x-ray technician must enter an x-ray technique, which factors in voltage, current, and time for the procedure, into the input apparatus 14. Instead of being entered by the first x-ray technician, the x-ray technique may be selected from a list of pre-programmed techniques in the first computer 15.

According to the digital medical imaging network system 70 as described in FIG. 2, the mobile x-ray apparatus 10 emits x-rays 60, which pass through the patient body area 40, and impact the sensors 48 in the flat panel detector 20. In the flat panel detector, the data is converted into digital signals. The sensors 48 can be direct or indirect sensors. The image data acquired by the flat panel detector 20 is automatically transmitted to the first computer 15, either by the flat panel detector cable 21, wireless transmitter receiver 38, or the media card 47. When using the media card 47, the image data is stored on the media card and then manually moved to the first computer 15 and inserted into the media slot 41.

Next, according to the digital medical imaging network system 70 described in FIG. 2, the display device 16 displays at least one digital image. The first x-ray technician preferably checks quality and position of the digital image on the display device 16. If the quality and position are unsatisfactory, the first x-ray technician may immediately make necessary adjustments and repeat the procedure. This is one of the primary advantages of the mobile x-ray apparatus 10 with its flat panel detector 20 over current x-ray devices. When the quality and position of the digital image is satisfactory, the first x-ray technician adds patient demographics using the keyboard 14, if not supplied by the imaging network. Other information about the procedure will be contained in a DICOM header, which accompanies the image information included in the study. This information is provided by the software in the first computer 15. The first x-ray technician may also select a network destination to which the patient study will be transmitted. Alternatively, the first x-ray technician selects a local storage medium 32 (e.g., CD, DVD, hard drive, etc.), on which to save the patient study 62.

Continuing with FIG. 2, the first computer 15 converts the patient study to Digital Imaging and Communications in Medicine (DICOM) protocol 23 and transmits it to the selected destination 64 via the facilities LAN (Local Area Network). If the network is wire-based, the digital medical imaging network system 70 preferably uses a local ethernet jack 13 and network cable 12. One end of the network cable 12 is removably inserted into the network cart jack on the first computer, and the opposite end of the network cable 12 is removably inserted in the network wall jack 13. If the LAN is wireless, the patient study is transmitted to the digital medical imaging network system 70, preferably using a facilities wireless network transmitter receiver 51, and the first computer uses a wireless network card 34.

The patient study is preferably sent to a Picture Archiving and Communication System (PACS) network 65. The PACS network 65 includes a DICOM quality control workstation 25, which comprises a second computer, a second display device, and appropriate image viewing software. A second x-ray technician verifies that the first x-ray technician properly matched the patient's image, the patient's demographics, and any other applicable information. If not, corrections are made in the patient study is sent to a DICOM archive 26.

The DICOM archive 26 is a storage device, more specifically, a computer running an archive software solution. It is preferably a Redundant Array of Independent Disk (RAID) 5 server with a large data capacity and a backup external storage device, for example, a tape, DVD, or CD jukebox. Alternatively, the archive 26 incorporates a Storage Area Network (SAN) or archive over the Internet to a remote location.

Continuing with FIG. 2, the patient study may be further routed to a review workstation 27 via the network. The review workstation 27 comprises a third computer, a third display device, and appropriate image viewing software. The review workstation 27 may be located in an emergency room (ER), so that ER medical personnel may quickly review the patient study and take immediate action. Another exemplary location of this review workstation 27 is a nursing station, where the patient study is accessible to a variety of hospital medical personnel, such as doctors, nurses, specialists, technologists, etc.

Moreover, the patient study may be routed to a diagnostic workstation 28, again via the network, for analysis by a radiologist or other specialist. The diagnostic workstation 28 comprises a number of high-resolution diagnostic display devices 30, a diagnostic computer, and appropriate image viewing software, so that the radiologist can examine, manipulate, and otherwise enhance the image. The high-resolution diagnostic display devices 30 may be LCD or CRT displays. The diagnostic workstation 28 enables the radiologist to alter the window, level, density, contrast, and magnification, and perform inversion of grayscale and other enhancements. After the radiologist analyzes the patient study, he or she can produce a report 29 for the referring clinician. The report can quickly be conveyed to the referring clinician through the network. The referring clinician can then review the report at his or her convenience 31.

Instead of transmitting the patient study to different parties through the wire-based or wireless network, the first x-ray technician may opt to save the patient study to the local storage medium 32. In order to save the patient study to the local storage medium 32, the first x-ray technician simply defines the local storage medium 32 as a destination and saved copies of the patient study are written to the hard drive, CD, DVD 33, etc. Thereafter, the patient study may be hand-carried, mailed, or otherwise sent to the appropriate medical personnel.

Several different combinations of means of communication between the computer 15 and flat panel detector 20 are possible. Two such combinations are depicted in FIGS. 7 and 8.

Figure 7:
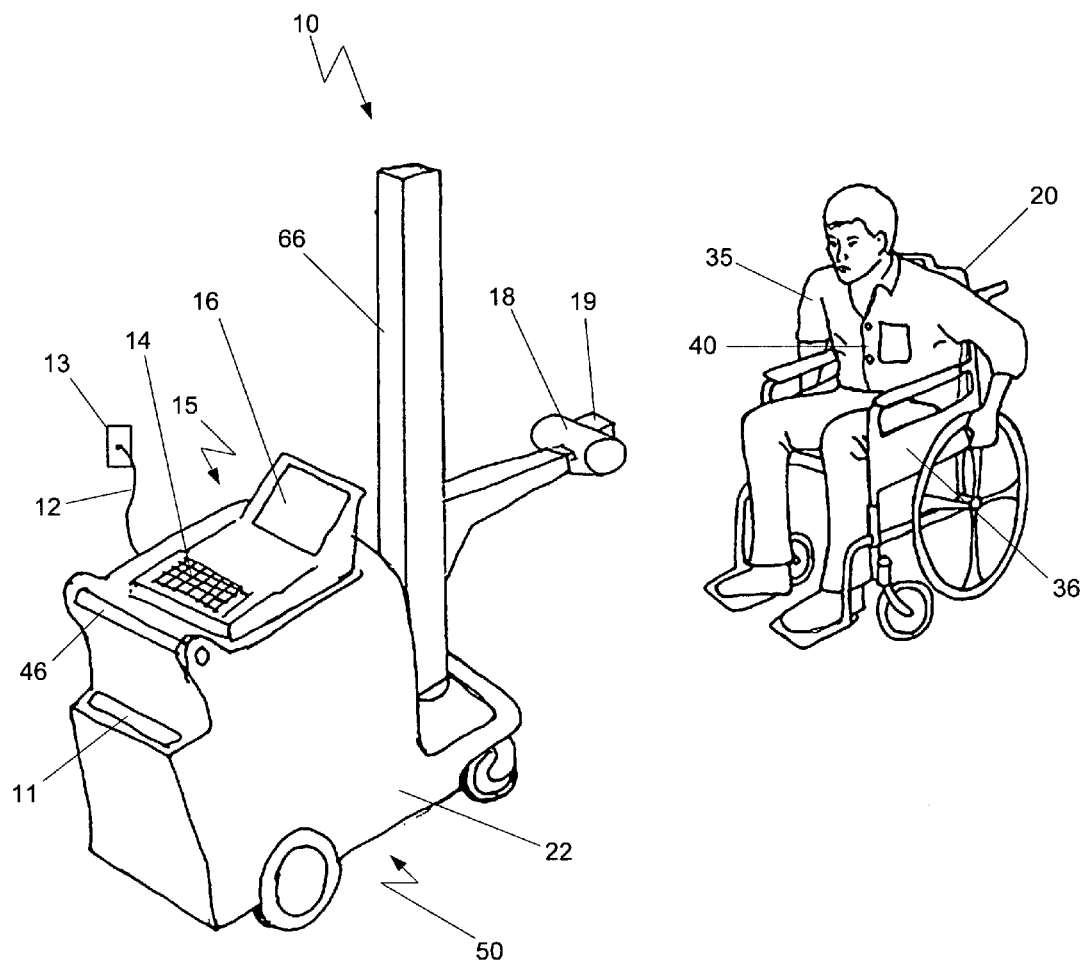
FIG. 7 is a perspective view of a mobile x-ray apparatus according to the present invention, showing a patient seated in a wheelchair with a wireless flat panel detector behind the patient's back.

In FIG. 7, the mobile x-ray apparatus 10 is shown in use with wireless transmitters or a data card for communication between the flat panel detector 20 and the first computer 15. The first computer 15 is connected to the network wall jack 13 by the network cable 12. The flat panel detector 20 is behind the patient's back. The flat panel detector 20 is not connected to the computer by a cable.

Figure 8:
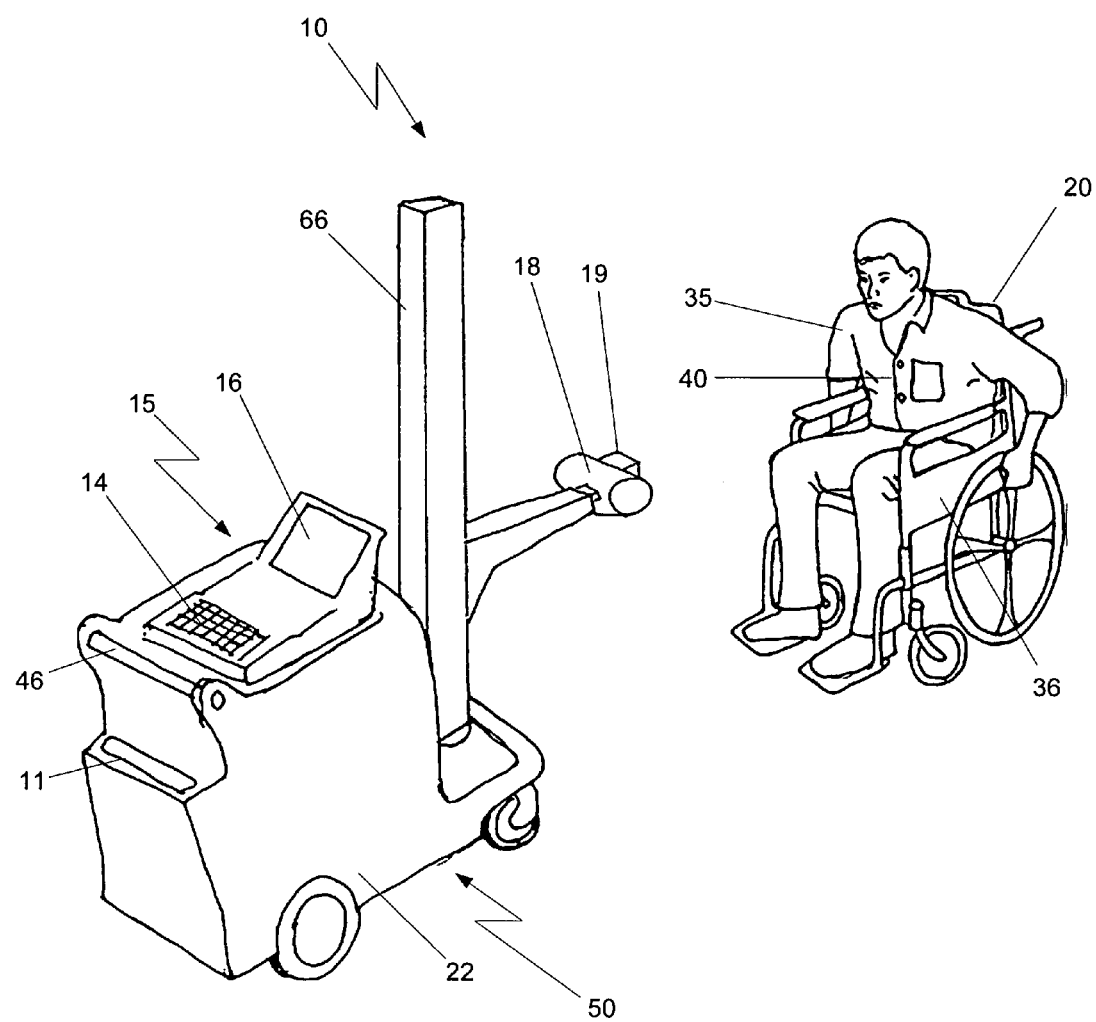
FIG. 8 is a perspective view of a wireless mobile x-ray apparatus according to the present invention, showing a patient seated in a wheelchair with a wireless flat panel detector behind the patient.

In FIG. 8, the mobile x-ray apparatus 10 is shown in use with a wireless transmitter receiver or a data card for communication between the flat panel detector 20 and the computer 15 and in communication with the medical imaging network using the facilities wireless network.

Also included herein is a method of rapidly generating a digital x-ray image and forwarding it to a remote site, which is shown in FIG. 2. The method comprises the steps of:

(a) moving a mobile x-ray apparatus 10 to the patient, and entering an imaging technique at the mobile x-ray apparatus;

(b) positioning a flat panel detector 20 of the mobile x-ray apparatus 10 under a target body area 40 of the patient;

(c) emitting x-rays from the mobile x-ray apparatus 10 onto the target body area 40;

(d) sensing energy from the x-rays using sensors 48 of the flat panel detector 20;

(e) converting signals from the sensors 48 of the flat panel detector 20 into at least one digital image;

(f) transmitting the digital image from the flat panel detector 20 to a first computer 15 of the mobile x-ray apparatus 10; and (g) forwarding the digital image to a remote site using the first computer 15; and wherein the at least one digital image is transmitted from the flat panel detector to the first computer by a wireless network.

Preferably, the digital image is transmitted from the flat panel detector 20 to the first computer 15 by a flat panel detector cable 21; a wireless network; or a media card 47. Normally, a first x-ray technician views the digital image on a first output device of the first computer 15. Then the first x-ray technician enters patient demographics via a first input apparatus 14 of the first computer 15. The digital image and the patient demographics form a patient study.

The method of the present invention preferably further comprises the following alternate or cumulative steps:

entering patient demographics via a first input apparatus 14 of the first computer 15; wherein the digital image and the patient demographics form a patient study. The first computer 15 optionally comprises a local storage medium 32 for saving the patient study.

converting the patient study to diagnostic imaging and communications for medicine (DICOM) protocol within the first computer 15.

transmitting the patient study to a first network destination via a network. The first network destination is preferably a DICOM quality control workstation 25 with a second computer and a second display device. The second computer and the second display device can be used to verify a match between the digital image and the patent demographics, and the patient study can then be transmitted to a second network destination via the network. The second network destination is preferably a DICOM archive 26. The second network destination can also be a review workstation 27 comprising a third computer and a third display device. Alternatively, the second network destination is a diagnostic workstation 28 comprising a diagnostic computer, a number of high-resolution diagnostic display devices, and image viewing software. The patient study further includes the steps of: analyzing the digital image using the image viewing software, and transmitting an x-ray report to a remote site via the network. The network is a wireless network or a wire-based network.

From the foregoing it can be realized that the described apparatus of the present invention may be easily and conveniently utilized as a mobile x-ray apparatus and system. It is to be understood that any dimensions given herein are illustrative, and are not meant to be limiting.

While preferred embodiments of the invention have been described using specific terms, this description is for illustrative purposes only. It will be apparent to those of ordinary skill in the art that various modifications, substitutions, omissions, and changes may be made without departing from the spirit or scope of the invention, and that such are intended to be within the scope of the present invention as defined by the following claims. It is intended that the doctrine of equivalents be relied upon to determine the fair scope of these claims in connection with any other person's product which fall outside the literal wording of these claims, but which in reality do not materially depart from this invention. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

BRIEF LIST OF REFERENCE NUMBERS USED
IN THE DRAWINGS

10 mobile x-ray apparatus
11 storage area
12 network cable
13 network wall jack
14 first input apparatus
15 first computer
16 first display device
17 patient support surface 18 x-ray tube
19 columnator
20 flat panel detector
21 flat panel detector cable
22 cart
23 patient study converted to DICOM protocol
24 network card
25 DICOM quality control workstation
26 DICOM archive
27 review workstation
28 diagnostic workstation
29 radiologist transcribes report
30 high-resolution diagnostic display device
31 radiologist report received and reviewed by clinician
32 local storage medium
33 patient study saved, copied, or written to local storage
34 wireless network card
35 patient
36 wheelchair
38 wireless transmitter receiver
39 computer support surface
40 target body area
41 media card slot
42 internal battery contact connector
44 small table
45 cart wheel
46 cart push bar
47 media card
48 sensors
49 flat panel detector handle
50 x-ray cart assembly
51 facilities network transmitter receiver
60 mobile x-ray machine emits x-rays
61 x-rays impact flat panel detector
63 flat panel detector cable port
64 DICOM data transmitted via network
65 PACS network
66 tube stand
70 digital medical imaging network system

What is claimed is:

1. A digital radiography method of rapidly generating a digital x-ray image and forwarding it to a remote site, the method comprising the steps of:
   (a) moving a mobile x-ray apparatus to the patient, and entering an imaging technique at the mobile x-ray apparatus;
   (b) positioning a flat panel detector of the mobile x-ray apparatus under a target body area of the patient;
   (c) emitting x-rays from the mobile x-ray apparatus onto the target body area;
   (d) sensing energy from the x-rays using sensors of the flat panel detector;
   (e) converting signals from the sensors of the flat panel detector into at least one digital image;
   (f) transmitting the at least one digital image from the flat panel detector to a first computer of the mobile x-ray apparatus;
   (g) forwarding the at least one digital image to a remote site using the first computer; and wherein the at least one digital image is transmitted from the flat panel detector to the first computer by a wireless network; and further comprising the step of using a first input apparatus of the first computer to enter patient demographics; wherein the at least one digital image and the patient demographics form a patient study; and further comprising the step of converting the patient study to Digital Imaging and Communications in Medicine protocol within the first computer prior to sending the patient study to a quality control workstation.

2. The method according to claim 1, further comprising the step of transmitting the patient study to a first network destination via a network.

3. The method according to claim 2, wherein the first network destination is a Digital Imaging and Communications in Medicine quality control workstation, the Digital Imaging and Communications in Medicine quality control workstation comprising a second computer and a second display device.

4. The method according to claim 3, further comprising the steps of: using the second computer and the second display device to verify a match between the at least one digital image and the patent demographics, and then transmitting the patient study to a second network destination via the network.

5. The method according to claim 4, wherein the second network destination is a Digital Imaging and Communications in Medicine archive.

6. The method according to claim 4, wherein the second network destination is a review workstation, the review workstation comprising a third computer and a third display device.

7. The method according to claim 4, wherein the second network destination is a Digital Imaging and Communications in Medicine diagnostic workstation, the diagnostic workstation comprising a diagnostic computer, a plurality of high-resolution diagnostic display devices, and image viewing software.

8. The method according to claim 7, further comprising the steps of: analyzing the at least one digital image displayed on at least one high-resolution monitor using the image viewing software, and transmitting an x-ray report to a remote site via the network.

9. The method according to claim 1, wherein the network is a wireless network.

* * * * *